(12) United States Patent
Al-Ali et al.

(10) Patent No.: US 7,254,431 B2
(45) Date of Patent: Aug. 7, 2007

(54) PHYSIOLOGICAL PARAMETER TRACKING SYSTEM

(75) Inventors: Ammar Al-Ali, Tustin, CA (US); Mohamed Diab, Mission Viejo, CA (US); Walter M. Weber, Laguna Hills, CA (US)

(73) Assignee: Masimo Corporation, Irvine, CA (US)

( * ) Notice: Subject to any disclaimer, the term of this patent is extended or adjusted under 35 U.S.C. 154(b) by 333 days.

(21) Appl. No.: 10/930,048

(22) Filed: Aug. 30, 2004

(65) Prior Publication Data

US 2005/0090724 A1   Apr. 28, 2005

Related U.S. Application Data

(60) Provisional application No. 60/498,749, filed on Aug. 28, 2003.

(51) Int. Cl.
*A61B 5/00* (2006.01)
(52) U.S. Cl. .................................. 600/323; 600/310
(58) Field of Classification Search ................ 600/309, 600/310, 322, 323, 336
See application file for complete search history.

(56) References Cited

U.S. PATENT DOCUMENTS

| | | | |
|---|---|---|---|
| 4,960,128 A | 10/1990 | Gordon et al. | |
| 5,163,438 A | 11/1992 | Gordon et al. | |
| 5,337,744 A | 8/1994 | Branigan | |
| 5,431,170 A | 7/1995 | Mathews | |
| 5,452,717 A | 9/1995 | Branigan et al. | |
| 5,482,036 A | 1/1996 | Diab et al. | |
| 5,490,505 A | 2/1996 | Diab et al. | |
| 5,494,043 A | 2/1996 | O'Sullivan et al. | |
| 5,533,511 A | 7/1996 | Kaspari et al. | |
| 5,590,649 A | 1/1997 | Caro et al. | |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,785,659 A | 7/1998 | Caro et al. | |
| 5,791,347 A | 8/1998 | Flaherty et al. | |
| 5,810,734 A | 9/1998 | Caro et al. | |
| 5,823,950 A | 10/1998 | Diab et al. | |
| 5,830,131 A | 11/1998 | Caro et al. | |
| 5,833,618 A | 11/1998 | Caro et al. | |
| 5,860,919 A | 1/1999 | Kiani-Azarbayjany et al. | |
| 5,890,929 A | 4/1999 | Mills et al. | |
| 5,904,654 A | 5/1999 | Wohltmann et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |

(Continued)

*Primary Examiner*—Eric F. Winakur
(74) *Attorney, Agent, or Firm*—Knobbe, Martens, Olson & Bear LLP

(57) ABSTRACT

A physiological parameter tracking system generates a reference parameter and a slowly varying parameter responsive to a physiological signal input. The slowly varying parameter is generated according to an update command. A physiological measurement output is provided that is responsive to a tracking function of the reference parameter and the slowly varying parameter.

19 Claims, 5 Drawing Sheets

U.S. PATENT DOCUMENTS

| | | |
|---|---|---|
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,334,065 B1 | 12/2001 | Al-Ali et al. |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Diab et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,725,075 B2 | 4/2004 | Al-Ali |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,990,426 B2 * | 1/2006 | Yoon et al. ................ 702/139 |

\* cited by examiner

PHYSIOLOGICAL PARAMETER TRACKING SYSTEM

The present application claims benefit of U.S. Provisional Application No. 60/498,749 filed on Aug. 28, 2003, entitled "*Physiological Parameter Tracking System.*" The present application incorporates the disclosure of the foregoing application herein by reference.

BACKGROUND OF THE INVENTION

Oxygen transport from the lungs to body tissue can be monitored by measuring various physiological parameters. For example, oxygen saturation of arterial blood ($S_aO_2$) is a measure of the ratio of oxyhemoglobin ($HbO_2$) concentration to the sum of $HbO_2$ and deoxyhemoglobin (Hb) concentrations in the arterial blood. Because $HbO_2$ is the major oxygen carrying component of blood, $S_aO_2$ is indicative of oxygen delivery to body tissues. As another example, oxygen saturation of venous blood ($S_vO_2$) is a similar measure of $HbO_2$ and Hb concentrations in venous blood and is indicative of oxygen consumption by body tissues. Measurements of the concentrations of carboxyhemoglobin (HbCO) and methemoglobin (MetHb) are indicative of abnormal hemoglobin constituents that interfere with oxygen transport.

Pulse oximetry is a noninvasive, easy to use, inexpensive procedure for measuring the oxygen saturation level of arterial blood. Pulse oximeters perform a spectral analysis of the pulsatile component of arterial blood in order to determine oxygen saturation ($S_{pa}O_2$), which is an estimate of $S_aO_2$. A pulse oximetry system has a sensor and a monitor. The sensor has emitters that typically consist of a red light emitting diode (LED) and an infrared LED that project light through blood vessels and capillaries underneath a tissue site, such as a fingernail bed. A sensor also has a detector that typically is a photodiode positioned opposite the LEDs so as to detect the emitted light as it emerges from the tissue site. A pulse oximetry sensor is described in U.S. Pat. No. 6,088,607 entitled "Low Noise Optical Probe," which is assigned to Masimo Corporation, Irvine, Calif. and incorporated by reference herein.

SUMMARY OF THE INVENTION

One aspect of a physiological parameter tracking system comprises a physiological signal input having first and second intensity signal components received from a light-sensitive detector that detects light of at least first and second wavelengths transmitted through body tissue carrying pulsing blood. The first and second intensity signal components are at least partially based on a pulse of the pulsing blood. A reference parameter is calculated in response to the physiological signal. Also, a slow parameter is generated in response to the physiological signal according to an update command. A physiological measurement output is generated in response to a tracking function of the reference parameter and the slowly varying parameter.

Another aspect of a physiological parameter tracking system is a method comprising the steps of inputting a physiological signal and calculating a reference parameter from the signal. Further steps include defining an update command, tracking the reference parameter according to the update command, and outputting a physiological measurement responsive to the tracking step.

A further aspect of a physiological parameter tracking system is a method comprising the steps of providing a physiological signal, calculating arterial oxygen saturation from the signal, and calculating a slowly varying parameter during a first period. Additional steps include holding the slowly varying parameter during a second period and outputting a physiological measurement responsive to the arterial oxygen saturation and the slowly varying parameter.

DETAILED DESCRIPTION OF THE PREFERRED EMBODIMENT

Overview

Figure 1:
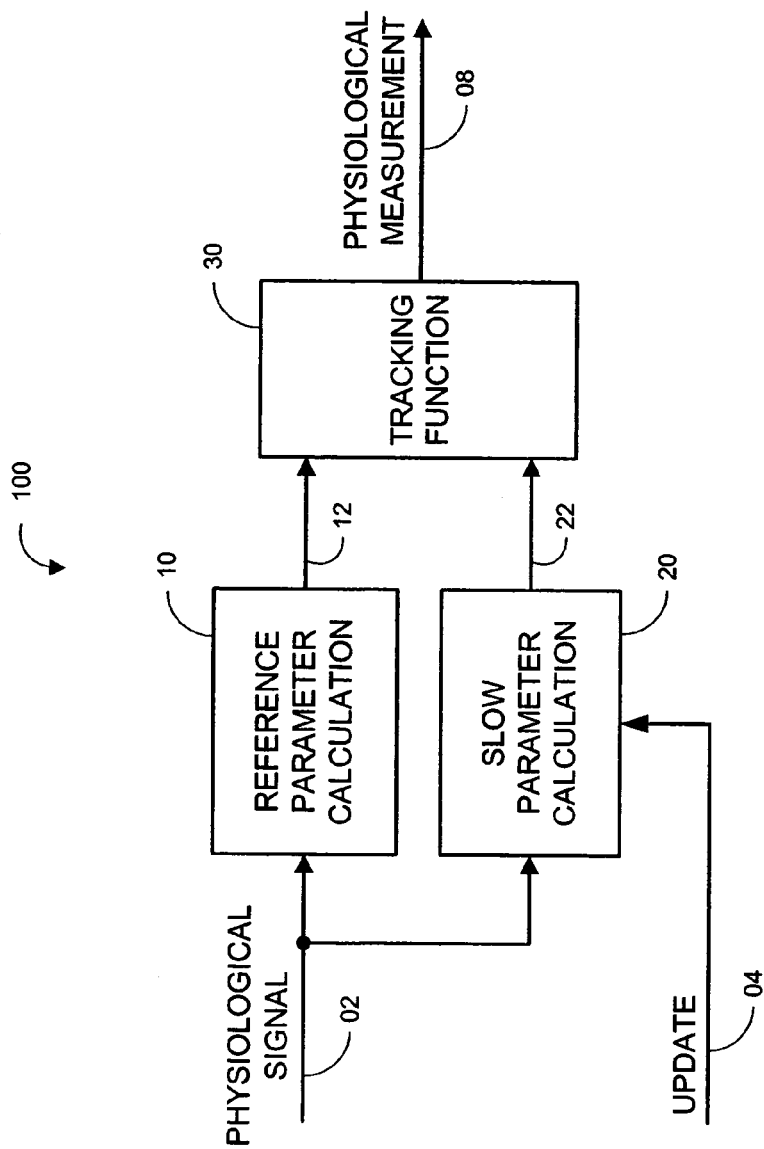
FIG. 1 is a block diagram of a slow parameter calculation embodiment of a physiological parameter tracking system.
Figure 4:
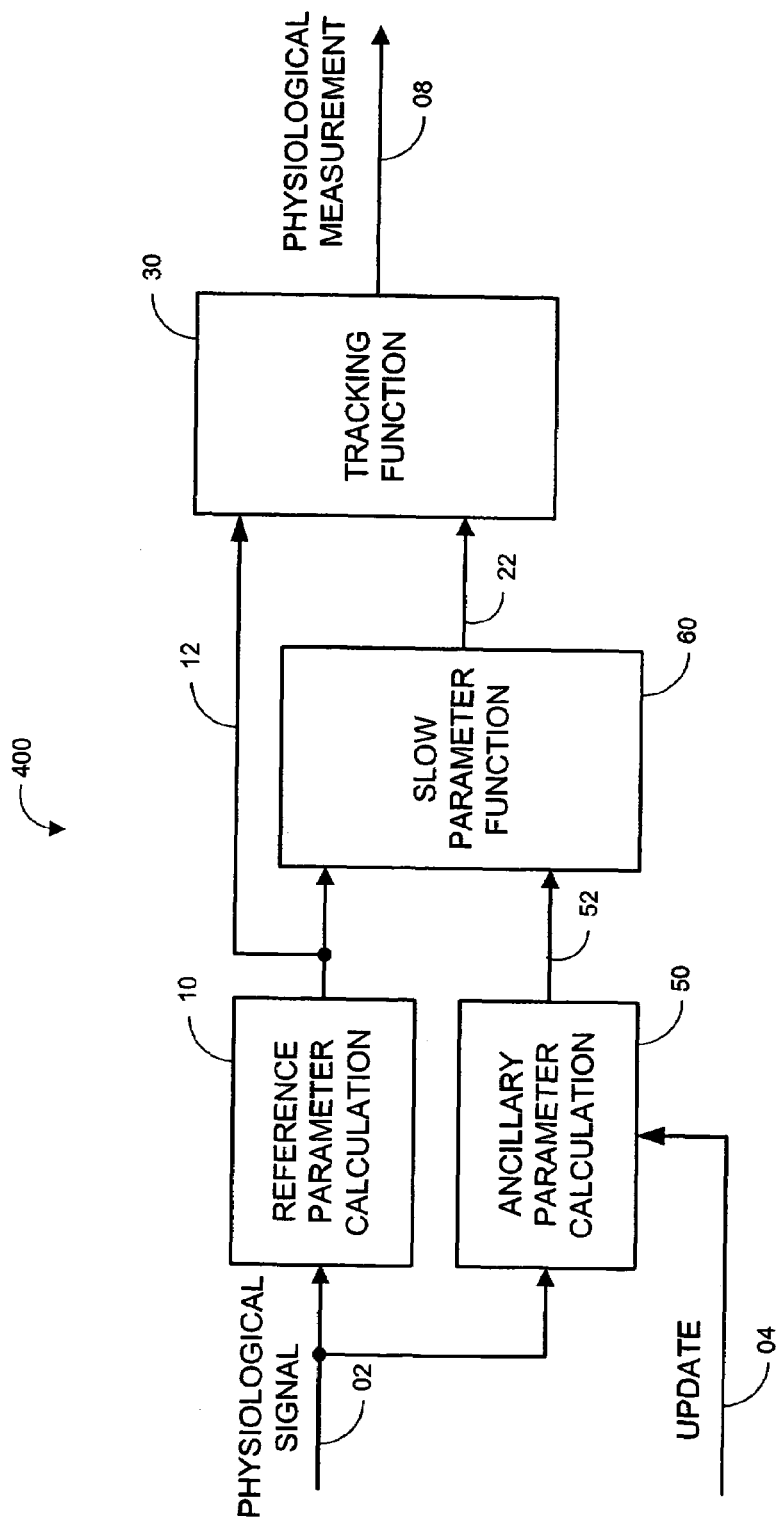
FIG. 4 is a block diagram of an ancillary calculation embodiment of a physiological parameter tracking system for operation in a S/H mode.
Figure 5:
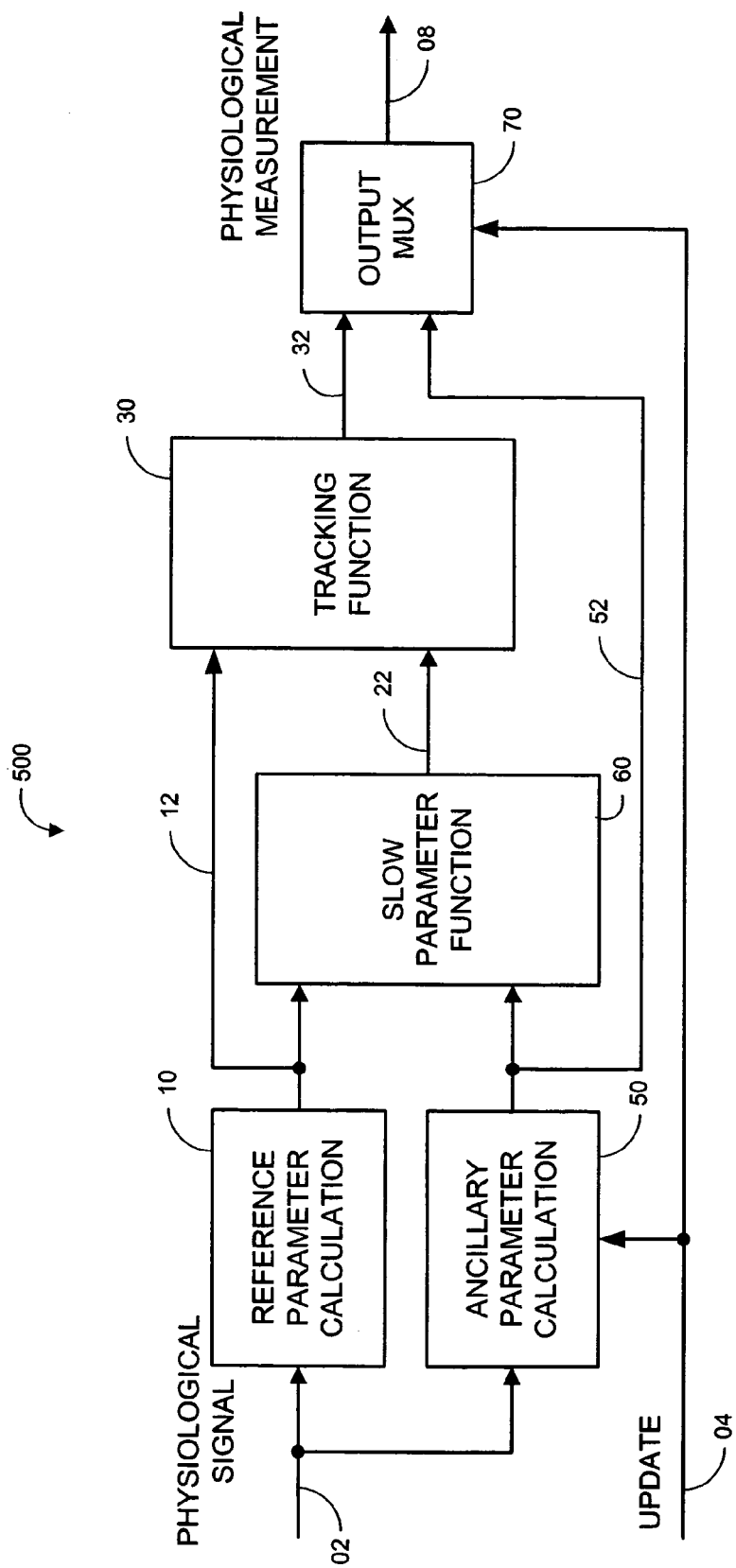
FIG. 5 is a block diagram of an ancillary calculation embodiment of a physiological parameter tracking system for operation in a T/H mode.

FIGS. 1, 4 and 5 illustrate embodiments of a physiological parameter tracking system that advantageously provide a clinically accurate physiological measurement by tracking a reference parameter based upon a slowly varying ("slow") parameter. As such, it is not necessary to continuously or frequently perform complex calculations to derive the physiological measurement. That is, the physiological measurement is a relatively simple function of the reference parameter and the slow parameter. Slow parameter calculations are performed only when conditions are favorable, or alternatively, suspended when conditions are not favorable, as indicated by an update command. The update command may be responsive to conditions such as power consumption goals or the quality of a physiological signal input to name a few.

In one embodiment, the slow parameter is HbCO or MetHb and the reference parameter is $S_{pa}O_2$. Accordingly, the physiological measurement is $S_{pa}O_2$ corrected for the presence of one or both of these abnormal hemoglobin constituents. In another embodiment, the slow parameter is $\Delta_{av}=S_{pa}O_2-S_vO_2$, a measure of oxygen consumption at a tissue site, and the reference parameter is $S_{pa}O_2$. Accordingly, the physiological measurement is an estimate of $S_vO_2$.

Slow Parameter Calculation

FIG. 1 illustrates a slow parameter calculation embodiment of a physiological parameter tracking system 100 in which the slow parameter 22 is derived from and responsive to a physiological signal 02. The physiological parameter tracking system 100 has a physiological signal 02 input, a reference parameter calculation 10, a slow parameter calculation 20 and a tracking function 30 and generates a physiological measurement 08 output. The reference parameter calculation 10 generates a reference parameter 12 from the physiological signal 02. The slow parameter calculation 20 generates the slow parameter 22 from the physiological signal 02 input. The tracking function 30 generates the physiological measurement 08 from the reference parameter 12 and the slow parameter 22.

As shown in FIG. 1, the physiological signal 02 is responsive to a physiological condition. In one embodiment, the physiological signal 02 originates from an optical sensor (not shown) attached to a tissue site. The sensor transmits multiple wavelengths of optical energy $\lambda_1, \lambda_2, \ldots, \lambda_n$ into the tissue site and detects corresponding optical energy emerging from the tissue site. The reference parameter calculation 10 may include pulse oximetry algorithms that operate on the physiological signal 02 to generate arterial oxygen saturation, $S_{pa}O_2$, as the reference parameter 12. A pulse oximetry signal processor and algorithms are described in U.S. Pat. No. 5,632,272 entitled Signal Processing Apparatus which is assigned to Masimo Corporation, Irvine, Calif. and incorporated by reference herein.

Also shown in FIG. 1, the slow parameter calculation 20 generates a slow parameter 22 from the physiological signal input 02 according to an update command 04. As an example, the slow parameter calculation 20 may include algorithms that operate on the physiological signal 02 to generate a measure of the concentration of abnormal hemoglobin, such as HbCO or MetHb. Multiple wavelength signal processing for measuring abnormal hemoglobin constituents, for example, is described in U.S. Provisional Patent Application No. 60/426,638 entitled "Parameter Compensated Physiological Monitor," U.S. Provisional Patent Application. No. 60/428,419 entitled "Blood Parameter Measurement System," and U.S. Pat. No. 6,229,856 entitled "Method and Apparatus for Demodulating Signals in a Pulse Oximetry System", which is assigned to Masimo Corporation, Irvine, Calif., all incorporated by reference herein.

Further shown in FIG. 1, the update command 04 may operate in a sample and hold (S/H) mode. That is, when the update command 04 is asserted, the slow parameter calculation 20 is triggered and the resulting slow parameter 22 value is held until a subsequent calculation. Operation of a physiological parameter tracking system having a S/H update is described with respect to FIG. 2, below. Alternatively, the update command 04 may operate in a track and hold (T/H) mode. That is, while the update command 04 is asserted, the slow parameter calculation 20 continues to generate values for the slow parameter 22. When the update command 04 is not asserted, the last generated value of the slow parameter 22 is held until the update command 04 is once more asserted. Operation of a physiological parameter tracking system having a T/H update is described with respect to FIG. 3, below.

Tracking Examples

Figure 2:
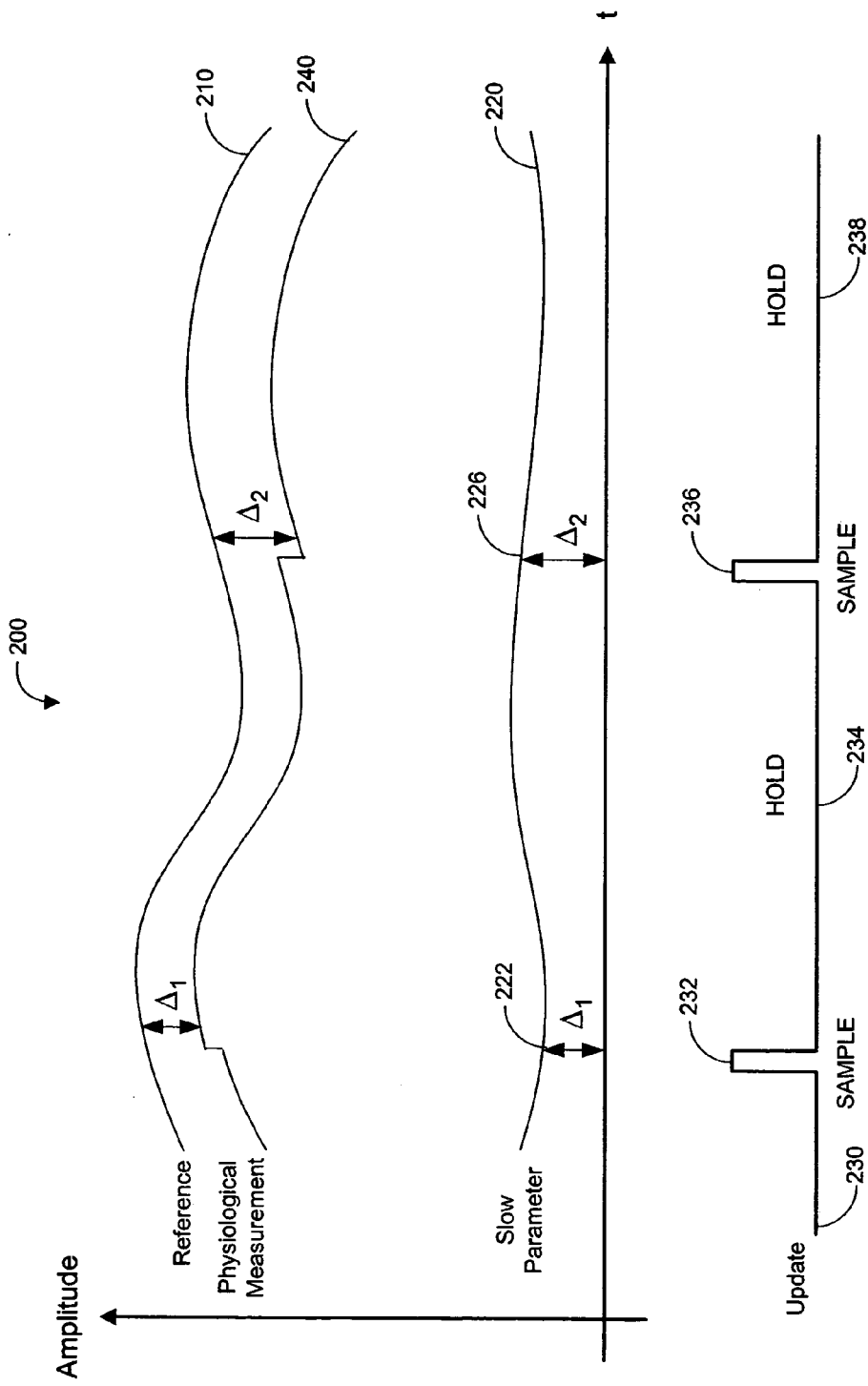
FIG. 2 is a graph illustrating operation of a physiological parameter tracking system in a sample and hold (S/H) mode.

FIG. 2 is an amplitude versus time graph 200 illustrating operation of a physiological parameter tracking system utilizing a S/H update. The graph 200 illustrates a reference curve 210 corresponding to a reference parameter 12 (FIG. 1) and a slow parameter curve 220 corresponding to a slow parameter 22 (FIG. 1). Below the graph 200 is a timing diagram 230 corresponding to the update command 04 (FIG. 1). A physiological measurement curve 240 corresponds to the physiological measurement 08 (FIG. 1).

As shown in FIG. 2, the physiological measurement curve 240 tracks the reference curve 210 according to a tracking function 30 (FIG. 1), which in this illustration is the difference between the reference parameter 12 (FIG. 1) and the slow parameter 22 (FIG. 1). A slow parameter 220 value is calculated at sample times 232, 236 and maintained throughout hold periods 234, 238. In particular, during a first sample time 232, a slow parameter value 222 of $\Delta_1$ is calculated, and during a second sample time 236, a slow parameter value 226 of $\Delta_2$ is calculated. As a result, during a first hold period 234, the physiological measurement curve 240 tracks the reference curve 210 by a difference of $\Delta_1$. Likewise, during a second hold period 238, the physiological measurement curve 240 tracks the reference curve 210 by a difference of $\Delta_2$. In this manner, the physiological measurement 240 is advantageously displayed with clinical accuracy utilizing only occasional computational resources and reducing power consumption accordingly.

Figure 3:
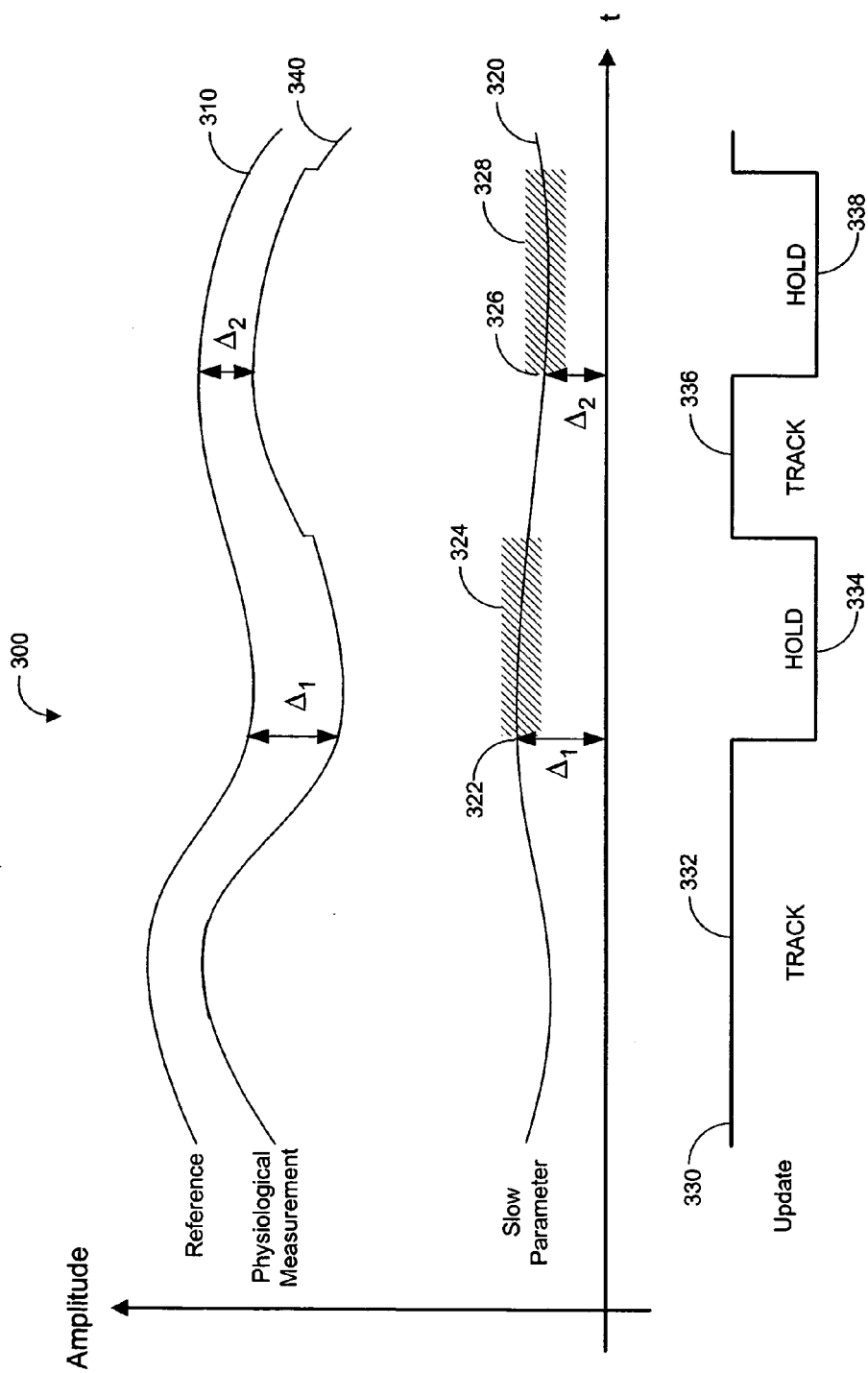
FIG. 3 is a graph illustrating operation of a physiological parameter tracking system in a track and hold (T/H) mode.

FIG. 3 is an amplitude versus time graph 300 illustrating operation of a physiological parameter tracking system utilizing a T/H update. The graph 300 illustrates a reference curve 310 corresponding to a reference parameter 12 (FIG. 1) and a slow parameter curve 320 corresponding to a slow parameter 22 (FIG. 1). Below the graph 300 is a timing diagram 330 corresponding to the update command 04 (FIG. 1). A physiological measurement curve 340 corresponds to the physiological measurement 08 (FIG. 1).

As shown in FIG. 3, the physiological measurement curve 340 tracks the reference curve 310 according to a tracking function 30 (FIG. 1), which, again, is the difference between the reference parameter 12 (FIG. 1) and the slow parameter 22 (FIG. 1). Slow parameter 320 values are calculated throughout track periods 332, 336, and the last computed values are maintained throughout the corresponding hold periods 334, 338. In particular, during a first track period 332, the physiological measurement curve 340 is the reference curve 310 minus the slow parameter curve 320. At the end of the first track period 332, a slow parameter value 332 of $\Delta_1$ is maintained throughout the first hold period 334. As a result, during the first hold period 334, the physiological measurement curve 340 is the reference curve 310 minus $\Delta_1$ and does not depend on the slow parameter curve 320. That is, during the first hold period 332, the physiological measurement curve 340 tracks the reference curve 310 by a difference of $\Delta_1$.

The "track" periods 332, 336 are so named because the slow parameter calculation 20 (FIG. 1) in response to the update timing 330 operates in a manner roughly analogous to a conventional track/hold amplifier when its output tracks the input. These are not to be confused with the periods when the physiological measurement curve 340 is "tracking" the reference parameter curve 310, which actually is during the hold periods 334, 338, when the slow parameter 22 (FIG. 1) output is held constant.

Also shown in FIG. 3, during a second track period 336, the physiological measurement curve 340 is again the reference curve 310 minus the slow parameter curve 320. At the end of the second track period 336, a slow parameter value 326 of $\Delta_2$ is maintained throughout the second hold period 338. As a result, during the second hold period 338, the physiological measurement curve 340 is the reference curve 310 minus $\Delta_2$ and does not depend on the slow parameter curve 320. That is, during the second hold period 338, the physiological measurement curve 340 tracks the reference curve 310 at a difference of $\Delta_2$.

Further shown in FIG. 3, the hold periods 334, 338 may correspond to slow parameter drop-out periods 324, 328, i.e. periods when the slow parameter cannot be accurately calculated. In this manner, the physiological measurement 340 is advantageously displayed with clinical accuracy even when noise or other signal corruption prevents measurement of the slow parameter 320.

Ancillary Parameter Calculation

FIG. 4 illustrates an ancillary parameter calculation embodiment of a physiological parameter tracking system 400 in which the slow parameter 22 is derived from an ancillary parameter 52 in S/H mode. The ancillary parameter 52, in turn, is derived from a physiological signal 02. That is, unlike the slow parameter calculation embodiment 100 (FIG. 1), the slow parameter 22 is only indirectly derived from and responsive to the physiological signal 02. The physiological parameter tracking system 400 has a physiological signal 02 input, a reference parameter calculation 10 and a tracking function 30, and, accordingly, generates a physiological measurement 08, similarly as described with respect to FIG. 1, above. However, in the ancillary calculation embodiment 400, the slow parameter 22 is a function 60 of the reference parameter 12 and/or an ancillary parameter 52. An ancillary parameter calculation 50 generates the ancillary parameter 52 from the physiological signal input 02 according to a S/H update command 04 input, such as described with respect to FIG. 2, above.

As an example, the ancillary parameter calculation 50 may include algorithms that operate on the physiological signal 02 to intermittently calculate venous oxygen saturation, $S_{pv}O_2$, as determined by a S/H update command 04. A corresponding slow parameter function 60 is the difference between an $S_{pa}O_2$ reference parameter 12 and the $S_{pv}O_2$ ancillary parameter 52 to yield a $\Delta_{av}$ slow parameter 22. Then, the tracking function 30 is a difference between the $S_{pa}O_2$ reference parameter 12 and the sampled $\Delta_{av}$ slow parameter 22 to generate a $S_{pv}O_2$' physiological measurement 08. That is, the physiological measurement 08 in this example advantageously provides a continuous measurement of venous saturation $S_{pv}O_2$' utilizing intermittent calculations of $S_{pv}O_2$. Apparatus and methods for determining $S_{pv}O_2$ from mechanical or ventilator induced perturbation of the venous blood volume are described in U.S. Pat. No. 5,638,816 entitled "Active Pulse Blood Constituent Monitoring" and U.S. Pat. No. 6,334,065 entitled "Stereo Pulse Oximeter," which are assigned to Masimo Corporation, Irvine, Calif. and are incorporated by reference herein. As another example, the ancillary parameter calculation 50 may include algorithms that operate on the physiological signal 02 to intermittently calculate abnormal hemoglobin concentration, such as HbCO and/or MetHb, as determined by a S/H update command 04.

FIG. 5 illustrates an ancillary parameter calculation embodiment of a physiological parameter tracking system 500 in which the slow parameter 22 is derived from an ancillary parameter 52 in T/H mode. The ancillary parameter 52, in turn, is derived from a physiological signal 02. The physiological parameter tracking system 500 has a physiological signal 02 input, a reference parameter calculation 10, an ancillary parameter calculation 50, a slow parameter function 60 and a tracking function 30, and, accordingly, generates a physiological measurement 08, similarly as described with respect to FIG. 4, above. However, in this ancillary calculation embodiment 500, the update command 04 operates in a track and hold mode, as described with respect to FIG. 3, above. Accordingly, the ancillary calculation embodiment 500 also has an output multiplexer 70 having the tracking function output 32 and the ancillary parameter 52 as inputs and the physiological measurement 08 as an output, as controlled by the update command 04 input. As such, the physiological measurement 08 is the ancillary parameter 52 during a track period 332, 336 (FIG. 3) of the update command 04 and is a function of the ancillary parameter 52 and the reference parameter 10 during a hold period 334, 338 (FIG. 3) of the update command 04. That is, the physiological measurement 08 is advantageously the ancillary parameter 52 except during a hold period, when the physiological measurement 08 tracks the reference parameter 12 according to the maintained value of the slow parameter 22.

As an example, the ancillary parameter calculation 50 may continuously calculate venous oxygen saturation, $S_{pv}O_2$, as determined by the update command 04 during track periods, and this calculation is provided as the physiological measurement 08. However, during hold periods of the update command 04, the physiological measurement 08 becomes $S_{pv}O_2$', i.e. the $S_{pa}O_2$ reference parameter 12 minus a maintained value of the $\Delta_{av}$ slow parameter 22. The physiological measurement 08 in this example advantageously provides a measurement of venous saturation that is continuous through drop-out periods.

A physiological parameter tracking system has been disclosed in detail in connection with various embodiments. These embodiments are disclosed by way of examples only and are not to limit the scope of the claims that follow. One of ordinary skill in the art will appreciate many variations and modifications.

What is claimed is:

1. A physiological parameter tracking system comprising:
   a physiological signal input having at least first and second intensity signal components received from a light-sensitive detector that detects light of at least first and second wavelengths transmitted through body tissue carrying pulsing blood, wherein the first and second intensity signal components are at least partially based on a pulse of the pulsing blood;
   a reference parameter calculator configured to output a reference parameter responsive to said physiological signal;
   a slow parameter calculator configured to output a slow parameter responsive to said physiological signal according to an update command; and
   a tracking function calculator configured to output a physiological measurement output responsive to said reference parameter and said slow parameter.

2. The physiological parameter tracking system according to claim 1 further comprising an ancillary parameter calculator configured to output an ancillary parameter responsive to said physiological signal, wherein said slow parameter calculator is configured to output said slow parameter, said slow parameter being responsive to said reference parameter and said ancillary parameter.

3. The physiological parameter tracking system according to claim 2 further comprising an output multiplexer configured to output said physiological measurement as being responsive to one of a tracking function output and said ancillary parameter according to said update command.

4. The physiological parameter tracking system according to claim 2 wherein said ancillary parameter comprises a measure of venous oxygen saturation, said reference parameter comprises a measure of arterial oxygen saturation, said slow parameter comprises a measure of oxygen consumption and said physiological measurement output is indicative of venous oxygen saturation.

5. The physiological parameter tracking system according to claim 1 wherein said slow parameter comprises a measure of abnormal hemoglobin, said reference parameter comprises a measure of oxygen saturation and said physiological measurement is indicative of oxygen saturation corrected for abnormal hemoglobin.

6. The physiological parameter tracking system according to claim 1 wherein said update command operates in at least one of a sample and hold mode and a track and hold mode.

7. The physiological parameter tracking system according to claim 1 wherein said physiological measurement output is responsive to a difference between said reference parameter and said slow parameter.

8. A physiological parameter tracking method comprising the steps of:
  inputting a physiological signal;
  calculating a reference parameter from said signal;
  defining an update command;
  tracking said reference parameter according to said update command; and
  outputting a physiological measurement responsive to said tracking step,
  wherein said defining step comprises the substeps of:
    indicating one of a sample period and a tracking period for calculating a slow parameter response to said signal; and
    indicating a hold period for maintaining a previous calculation of said slow parameter.

9. The physiological parameter tracking method according to claim 8 wherein said tracking step comprises the substep of deriving a tracking function output from said reference parameter and said slow parameter.

10. The physiological parameter tracking method according to claim 9 further comprising the step of calculating an ancillary parameter from said signal.

11. The physiological parameter tracking method according to claim 10 wherein said outputting step comprises the substep of multiplexing said tracking function output and said ancillary parameter according to said update command.

12. The physiological parameter tracking method according to claim 11 wherein said ancillary parameter is venous oxygen saturation and said physiological measurement is said venous oxygen saturation during said tracking period and an estimate of venous oxygen saturation during said hold period.

13. The physiological parameter tracking method according to claim 10 wherein said ancillary parameter is a measure of abnormal hemoglobin.

14. The physiological parameter tracking method according to claim 13 wherein said physiological measurement is arterial oxygen saturation corrected for said abnormal hemoglobin.

15. A physiological parameter tracking method comprising the steps of:
  providing a physiological signal;
  calculating arterial oxygen saturation from said signal;
  calculating a slowly varying parameter during a first period;
  holding said slowly varying parameter during a second period; and
  outputting a physiological measurement responsive to said arterial oxygen saturation and said slowly varying parameter.

16. The physiological parameter tracking method according to claim 15 wherein said slowly varying parameter is abnormal hemoglobin concentration and said physiological measurement is said arterial oxygen saturation corrected for said abnormal hemoglobin concentration.

17. The physiological parameter tracking method according to claim 15 wherein said slowly varying parameter is a difference between said arterial oxygen saturation and venous oxygen saturation and said physiological measurement is said venous oxygen saturation during said first period and a venous oxygen saturation estimate during said second period.

18. The physiological parameter tracking method according to claim 15 wherein said calculating a slowly varying parameter step comprises the substeps of:
  indicating favorable conditions with an update command; and
  sampling said slowly varying parameter in response to said command.

19. The physiological parameter tracking method according to claim 15 wherein said holding step comprises the substeps of:
  indicating unfavorable conditions with an update command; and
  holding said slowly varying parameter in response to said command.

* * * * *

UNITED STATES PATENT AND TRADEMARK OFFICE
CERTIFICATE OF CORRECTION

PATENT NO. : 7,254,431 B2  Page 1 of 1
APPLICATION NO. : 10/930048
DATED : August 7, 2007
INVENTOR(S) : Ammar Al-Ali et al.

It is certified that error appears in the above-identified patent and that said Letters Patent is hereby corrected as shown below:

At column 5, line 31 (Approx.), please delete "ventillator" and insert -- ventilator --, therefor.

Signed and Sealed this

Fifth Day of August, 2008

JON W. DUDAS
*Director of the United States Patent and Trademark Office*